United States Patent [19]

Foley

[11] Patent Number: 4,471,067
[45] Date of Patent: Sep. 11, 1984

[54] DIMERIC CARBONYLATION OF 1,3-ALKADIENE

[75] Inventor: Paul Foley, Summit, N.J.

[73] Assignee: Celanese Corporation, New York, N.Y.

[21] Appl. No.: 505,006

[22] Filed: Jun. 16, 1983

Related U.S. Application Data

[62] Division of Ser. No. 319,818, Nov. 9, 1981, Pat. No. 4,416,823.

[51] Int. Cl.$^3$ ............................................. B01J 31/24
[52] U.S. Cl. ................................................... 502/162
[58] Field of Search ......................................... 502/162

[56] References Cited

U.S. PATENT DOCUMENTS

| | | | |
|---|---|---|---|
| 3,947,495 | 3/1976 | Murie et al. | 502/162 X |
| 4,246,183 | 1/1981 | Knifton | 502/162 X |
| 4,292,437 | 9/1981 | Squire et al. | 502/162 X |

Primary Examiner—Patrick Garvin
Attorney, Agent, or Firm—Depaoli & O'Brien

[57] ABSTRACT

This invention provides a process for dimeric hydroesterification of 1,3-alkadiene in the presence of a catalyst which is a stabilized complex of palladium, tertiary phosphine ligand and thiol compound.

2 Claims, No Drawings

DIMERIC CARBONYLATION OF 1,3-ALKADIENE

This is a division of application Ser. No. 319,818 filed Nov. 9, 1981 and now U.S. Pat. No. 4,416,823.

BACKGROUND OF THE INVENTION

Catalytic carbonylation of olefinic and acetylenic compounds to form oxygenated derivatives with an increased content of carbon atoms is a well-established technology. Various developments and improvements are described in United States patents such as U.S. Pat. Nos. 2,768,968; 2,863,911; 2,876,254; 3,040,090; 3,455,989; 3,501,518; 3,507,891; 3,652,655; 3,660,439; 3,700,706; 3,723,486; 3,746,747; 3,755,419; 3,755,421; 3,793,369; 3,856,832; 3,859,319; 3,887,595; 3,906,015; 3,917,677; 3,952,034; 3,992,423; 4,102,920; 4,245,115; 4,246,183; and references cited therein.

Of particular interest with respect to the present invention is the chemical literature relating to dimeric carbonylation of aliphatic conjugated dienes in the presence of a hydroxylated coreactant and a catalyst complex of a Group VIII noble metal and a Group VA tertiary donor ligand. The dimeric carbonylation reaction is illustrated by the following chemical equation with respect to the interaction of 1,3-butadiene with alkanol:

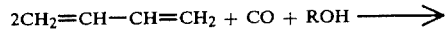

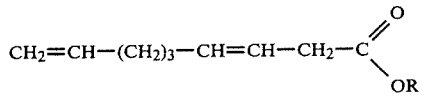

In a report published in Tetrahedron, 28, 3721 (1972), there is described a dimeric carbonylation of 1,3-butadiene in the presence of alkanol and a palladium-phosphine complex catalyst to yield alkyl 3,8-nonadienoate. The publication discloses that the absence of halide coordinated to the palladium metal is essential for the formation of alkyl nonadienoate product. In the presence of halide, one mole of 1,3-butadiene reacts with one mole of carbon monoxide and one mole of alkanol to yield alkyl 3-pentenoate.

U.S. Pat. No. 4,124,617 describes a process for the selective production of fatty acid derivatives from aliphatic diene substrates, in the presence of dual-function homogeneous palladium complexes and certain classes of organic tertiary nitrogen bases. One aspect of this type of process is that the use of tertiary nitrogen bases promotes the production of various byproducts such as $C_5$-esters. Another aspect is that the catalyst tends to exhibit a reaction rate decrease during the course of the carbonylation reaction due to instability of the catalyst system.

Further, in processes for dimeric carbonylation of aliphatic conjugated dienes such as are disclosed above, the dimeric product is separated from the catalyst complex and other components of the reaction product mixture employing conventional technique such as distillation. In such product recovery procedures some of the catalyst complex (e.g., palladium-phosphine complex) is lost by precipitation, and more significantly, the catalyst complex invariably suffers from a loss of reactivity. This is a serious consequence for purposes of a catalyst complex which is intended to be recovered and recycled in a dimeric carbonylation process. The efficiency of the process is dependent on the stability and reactivity of the catalyst system.

Accordingly, it is a main object of this invention to provide an improved process for conversion of aliphatic conjugated dienes into fatty acid derivatives.

It is another object of this invention to provide a process for producing alkyl nonadienoate by dimeric carbonylation of 1,3-alkadiene with improved conversion and selectivity.

It is a further object of this invention to provide a stabilized palladium catalyst solution adapted for carbonylation of olefinic hydrocarbons.

Other objects and advantages of the present invention shall become apparent from the accompanying description and illustrative processing data.

DESCRIPTION OF THE INVENTION

One or more objects of the invention are accomplished by a process for dimeric hydroesterification of 1,3-alkadiene which comprises (1) reacting 1,3-alkadiene with carbon monoxide and alkanol in a liquid medium containing a stabilized halide-free catalyst complex of palladium salt, tertiary phosphine ligand and thiol compound; and (2) recovering dimeric alkyl alkadienoate product.

The term "1,3-alkadiene" is meant to include acyclic 1,3-diene compounds which contain between about 4–12 carbon atoms, and which can contain other heteroatoms such as oxygen, sulfur, nitrogen and halogen which do not interfere with the invention process carbonylation. Illustrative of suitable 1,3-alkadiene compounds are 1,3-butadiene; 2-methyl-1,3-butadiene; 2,3-dimethyl-1,3-butadiene; 2-chloro-1,3-butadiene; 1,3-pentadiene; 5-phenyl-1,3-pentadiene; 1,3-hexadiene; 1,3-decadiene; and the like.

The present invention process is particularly adapted for converting a linear 1,3-alkadiene into a dimeric hydroesterification product with a high selectivity ratio of straight chain to branched chain product (e.g., a ratio of at least 9:1).

Further, under optimal conditions 1,3-butadiene is at least 80 percent converted, and the selectivity to alkyl nonadienoate product is at least 80 mole percent, based on the total moles of conversion products.

The term "alkanol" is meant to include primary, secondary and tertiary aliphatic alcohols which are suitably reactive under the carbonylation conditions. The alkanol reactant can be employed in essentially any proportion as dictated by practical considerations, e.g., at least about 0.5 moles of alkanol per mole of 1,3-alkadiene charged. A large excess of alkanol (e.g., up to about 10 moles per mole of 1,3-alkadiene) is employed if the alkanol is to function also as a solvent medium.

Illustrative of suitable alkanols are primary, secondary and tertiary alkanol reactants containing between about 1-12 carbon atoms and between about 1-4 hydroxyl groups, such as methanol, ethanol, 2-chloroethanol, 2-propanol, t-butanol, pentanol, cyclohexanol, decanol, dodecanol, ethyleneglycol, glycerine, 1,4-butanediol, pentaerythritol, trimethanolpropane, and the like.

It is preferred that the carbon monoxide is introduced into the process reaction system up to a partial pressure of between about 100 and 2000 psi of carbon monoxide. The carbon monoxide environment in the process system can contain one or more inert gases such as nitrogen, helium, argon, and the like. For optimal results it is essential that the process is conducted in a deoxygenated environment, so as not to affect adversely the 1,3-alkadiene conversion rate and the selective yield of alkyl nonadienoate product.

The liquid medium in the first step of the process can include a solvent diluent, in addition to the other liquid constituents in the carbonylation reaction system. Suitable solvents include propane, butane, pentane, cyclopentane, hexane, cyclohexane, heptane, octane, tetradecane, petroleum refinery light hydrocarbon mixtures, benzene, chlorobenzene, nitrobenzene, toluene, xylene, mesitylene, tetrahydrofuran, dimethylformamide, methyl ethyl ketone, product ester, and the like.

An important aspect of the present invention is the provision of a stabilized catalyst which is highly selective for dimeric carbonylation of aliphatic conjugated diene compounds. Thus, in a further embodiment the present invention provides a catalyst composition consisting of a solvent solution of solute components comprising a halide-free complex of palladium salt and tertiary phosphine ligand which is in contact with a stabilizing quantity of thiol compound.

The "solvent" in the said catalyst composition can comprise an inert solvent diluent of the type previously described, and/or 1,3-alkadiene, and/or alkanol, and/or tertiary phosphine, and the like. The said catalyst composition can be preformed prior to introduction into a carbonylation reaction zone, or it can be formed in situ by the separate introduction of the palladium salt, tertiary phosphine ligand and thiol components into the carbonylation reaction zone.

The palladium precursor compound preferably is in the form of a palladium-containing compound such as palladium acetate, palladium propionate, palladium acetylacetonate, palladium nitrate, palladium sulfate, bis-(1,5-diphenyl-3-pentadienone) palladium(o) and the like, with the exclusion of any halide-containing salts such as palladium(II) chloride.

With reference to the tertiary phosphine ligand, the term "phosphine" is meant to include corresponding phosphite derivatives. Illustrative of suitable tertiary phosphine ligands are triisopropylphosphine, tri-n-butylphosphine, triisobutylphosphine, tricyclohexylphosphine, triphenylphosphine, tritolylphosphine, tribenzylphosphine, and the corresponding phosphite compounds. The substituents in the tertiary phosphine ligands can be the same or different, and mixtures of tertiary phosphine ligands can be employed. Illustrative of a ligand mixture is one containing about 70–99 mole percent trialkylphosphine (e.g., triisopropylphosphine) and about 1–30 mole percent triarylphosphine (e.g., triphenylphosphine). A preferred class of tertiary phosphine ligands are trialkylphosphines in which each alkyl group contains between 2 and about 8 carbon atoms.

An essential aspect of the present invention catalyst system is the inclusion of a thiol compound in the catalyst composition or in the carbonylation reaction system in a quantity sufficient to stabilize the catalyst complex of palladium salt and tertiary phosphine ligand. The stabilizing agent can be any compound which contains one or more thiol groups, and which is soluble in the liquid reaction medium in the carbonylation zone.

A preferred class of thiol compounds is that corresponding to the formula:

R-SH where R is an aliphatic, alicyclic or aromatic substituent containing between about 1–30 carbon atoms.

Illustrative of suitable thiol compounds are methanethiol, ethanethiol, 1,1-dimethylethanethiol, 1-methylpropanethiol, 1-butanethiol, 1-tridecanethiol, cyclohexanethiol, benzenethiol, 1,4-butanedithiol, and the like.

The catalyst complex of palladium salt/tertiary phosphine/thiol compound is provided in the carbonylation reaction medium in at least a catalytic quantity, and the mole ratio of 1,3-alkadiene to catalyst complex preferably is at least 25:1.

The palladium and tertiary phosphine ligand in the carbonylation zone liquid reaction medium typically are provided in a ratio between about 1–12 moles of tertiary phosphine ligand per gram atom of palladium metal.

The palladium and thiol compound in the carbonylation zone liquid reaction medium typically are provided in a ratio between about 1–20 moles of thiol compound per gram atom of palladium metal. If a large excess of thiol compound is employed, then there is formation of $C_5$ thioloate ester in place of alkanol-derived dimeric hydroesterification product.

It is highly preferred that the dimeric carbonylation step of the invention process is conducted in the presence of a vinyl polymerization inhibitor, e.g., hydroquinone. If an inhibitor is not included in the reaction system then there is an increased incremental loss of 1,3-alkadiene to polymeric byproducts. When a polymerization inhibitor is employed, the yield of byproducts can be limited to less than about 5 percent. The byproducts produced during 1,3-butadiene dimeric carbonylation, for example, include alkyl 3-pentenoate; vinylcyclohexene; 1,3,7-octatriene; 1-methoxy-3,7-octadiene; and oligomeric polyenes.

The temperature for the first step dimeric carbonylation reaction can vary in the range between about 0° C. and 150° C., and preferably is in the range between about 80° C. and 120° C.

The pressure in the first step reaction zone can vary in the range between about 300 and 2000 psi, and preferably is in the range between about 400 and 750 psi. As previously indicated, it is advantageous to provide a carbon monoxide partial pressure in the range between about 100 and 2000 psi in the first step reaction zone.

In a typical batch type process, the reaction time for the dimeric carbonylation step will average in the range between about 2 and 25 hours, as determined by temperature and pressure parameters and the reactivity of the palladium-phosphine-thiol complex catalyst.

After the completion of the first step dimeric carbonylation reaction, the liquid product mixture is cooled to room temperature or lower. Any high molecular weight polyene byproducts in the reaction product mixture tend to precipitate out during the cooling stage. As necessary, the reaction product mixture can be filtered to remove polymeric precipitate.

The product mixture is then fractionated by a conventional method such as distillation to recover the alkyl alkadienoate product. It is highly advantageous to leave some alkyl alkadienoate as a residual solvent medium for the catalyst complex which is in solution. The said solvent solution of catalyst can be recycled to the carbonylation step of the process.

In a batch type process, it is convenient and advantageous to perform several dimeric carbonylation runs successively in the same reactor system, without recovery of alkyl alkadienoate product between the respective runs. The accumulated product is recovered after the completion of the last run.

In another embodiment, this invention contemplates a continuous process for producing and recovering alkyl alkadienoate. Illustrative of a specific application of the continuous process, a solution of palladium-phosphine-thiol complex and alkanol is fed continuously to a first reaction zone of an elongated reactor system, simultaneously with the introduction of 1,3-butadiene. In the first reaction zone, the feed materials are admixed efficiently with each other and with carbon monoxide which is present at a partial pressure of at least 100 psi (e.g., 400–1000 psi). The admixture is passed into a second reaction zone of the reactor system, in which zone there is no input of additional carbon monoxide. The temperature and flow rates are controlled in the second reaction zone so that optimal proportions of 1,3-butadiene and carbon monoxide are reacted. The presence of incremental carbon monoxide is maintained in the second reaction zone in a quantity sufficient to prevent the formation of alkoxyoctadiene byproducts, but not sufficient to favor the formation of palladium poly-carbonyl and poly-palladium carbonyl complex species.

A product stream is removed continuously from the end of the second reaction zone. The product stream is distilled to remove a portion of the alkyl nonadienoate product. The residual solution of product and catalyst is recycled to the first reaction zone of the dimeric hydroesterification system.

The following examples are further illustrative of the present invention. The reactants and other specific ingredients are presented as being typical, and various modifications can be devised in view of the foregoing disclosure within the scope of the invention.

EXAMPLE I

This Example illustrates the preparation of a stabilized catalyst composition.

Into a nitrogen-flushed flask are charged sequentially palladium(II) acetate (0.9 gram, 4.0 moles), 20 milliliters of dry deoxygenated tetrahydrofuran, triisopropylphophine, (0.7 gram, $4.5 \times 10^{-3}$ mole) and 0.5 gram of hydroquinone. Upon stirring this mixture at room temperature for 15 minutes, a deep red-brown solution results. The tetrahydrofuran is removed on a rotary evaporator at <50° C. leaving a red-brown solid, which constitutes a standard catalyst composition in accordance with the present invention.

EXAMPLE II

This Example illustrates the dimeric hydroesterification of 1,3-butadiene.

A nitrogen-flushed stainless steel cylinder is charged with a standard catalyst composition (in accordance with Example I), dissolved in 0.46 mole of methanol, and with 0.093 mole of 1-butanethiol, 4.0 mmoles of triisopropylphosphine, and 0.048 mole of tetradecane (as a g.c. internal standard).

Into a second cylinder is placed 0.926 mole of 1,3-butadiene. The two cylinders are installed into a reactor system which allows injection of these solutions into an autoclave reactor using carbon monoxide pressure.

A 300 milliliter 316 SS magnadrive autoclave is evacuated to 0.1 torr to remove any volatile impurities, flushed with carbon monoxide and then charged at room temperature with the catalyst solution employing 100 psia of carbon monoxide. The 1,3-butadiene is charged into the autoclave reactor employing 500 psia of carbon monoxide. Reactor temperature is brought to 100° C. as quickly as possible (about one half hour) and stabilized at this temperature. Reactor pressure is maintained at 750 psia using carbon monoxide fed from a one liter storage vessel.

The reaction is followed as a function of time by observing both the change in pressure in the one liter storage vessel and the appearance of products by g.c. A one milliliter sample is taken from a bottom liquid sampling tap on the autocalve at a given time. This sample line is washed with pentane and flushed with nitrogen after each sample is taken.

After 21 hours of reaction time, a 70 percent 1,3-butadiene conversion is observed with a 48 percent yield of methyl 3,8-nonadienoate (0.224 mole). Other conversion products detected are 4-vinylcyclohexane (0.01 mole), 3,5,7-octatriene (0.011 mole), cyclooctadiene (0.013 mole), 1-butyl 3-thiolopentenoate (0.029 mole), 1-butyl thiolononadienoate (0.03 mole) and methyl 3-pentenoate (0.04 mole). No visible palladium black is observed in the reaction system.

EXAMPLE III

The procedure is the same as Example II, except that 5.3 mmoles of 1-butanethiol, a 125° C. reaction temperature and a 350 psi reactor pressure are employed.

After 26 hours of reaction time, a 75 percent yield of methyl 3,8-nonadienoate (based on initial 1,3-butadiene charged) is produced, at an STY of 219 grams of methyl 3,8-nonadienoate per liter hour (at 0–50 percent butadiene conversion). Other products observed are methyl 3-pentenoate (0.2 percent), 4-vinylcyclohexene (1.9 percent) and 1,5-cyclooctadiene (4.4 percent). No visible palladium black is observed in the reaction system.

What is claimed is:

1. A catalyst composition consisting of a solvent solution of solute components comprising a halide-free complex of palladium and tertiary phosphine ligand which is in contact with a stabilizing quantity of thiol compound.

2. A catalyst composition consisting of a solvent solution of solute components comprising a halide-free complex of palladium and tertiary phosphite ligand which is in contact with a stabilizing quantity of thiol compound.

* * * * *